United States Patent
Cheng (12)

(10) Patent No.: US 6,200,569 B1
(45) Date of Patent: Mar. 13, 2001

(54) COMPOSITION AND METHOD FOR INCREASING INSULIN ACTIVITY

(75) Inventor: Nanzheng Cheng, Beijing (CN)

(73) Assignee: Tang-An Medical Co., Ltd., Beijing (CN)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/965,051

(22) Filed: Nov. 5, 1997

(51) Int. Cl.[7] ............................ A61K 35/78; A61K 38/28
(52) U.S. Cl. ............................ 424/195.1; 424/655; 514/3; 514/866; 530/371
(58) Field of Search ............................ 424/195.1, 655; 514/3, 866; 530/371

(56) References Cited

U.S. PATENT DOCUMENTS

| | | |
|---|---|---|
| 4,315,927 | 2/1982 | Evans . |
| 5,175,156 | 12/1992 | Boynton et al. . |
| 5,522,175 | 6/1996 | Holtz . |
| 5,531,991 | 7/1996 | Cheng et al. . |
| 5,607,679 | 3/1997 | Rhodes . |
| 5,639,470 | 6/1997 | Ishibashi et al. . |
| 5,886,029 | * 3/1999 | Dhaliwal ........................ 424/195.1 |

FOREIGN PATENT DOCUMENTS

| | | |
|---|---|---|
| 50034100 | 11/1975 | (JP) . |
| 362077329 | * 4/1987 | (JP) . |
| 4-210644 | 7/1992 | (JP) . |
| 7-002688 | 1/1995 | (JP) . |
| 409275979 | * 10/1997 | (JP) . |
| WO 95/30427 | 11/1995 | (WO) . |

OTHER PUBLICATIONS

Swanston–Flatt et al. Diabetes Res. vol. 10, pp. 69–73, 1989.*

Ahmad et al. Ind. J. Biochem. Biophys. vol. 21, pp. 237–240, 1984.*

Gray et al. Proc. Nutrit. Soc. vol. 53, p. 125A, 1994.*

Ahmad et al. Acta Diab. Lat. vol. 21, pp. 349–355, 1984.*

Peasant et al. J. Biol. Chem. vol. 247 (21), pp. 6937–6945, 1972.*

Ewart et al. Diabetes. vol. 24, pp. 705–714, 1975.*

Kimura et al. Planta Med. vol. 53 (2), pp. 128–131, 1987.*

Anderson et al., (1979) *Elsevier/North–Holland Biomedical Press Chromium in Nutrition and Metabolism*, Shapcott and Hubert (eds.,).

Anderson, Richard A. (1995) *Journal of Advancement in Medicine* 8(1):37–50.

Berrio et al. (1992) *Horm Res* 37:225–229.

Cheng et al. (vol. 2, No. 5, Mar. 20, 1988) *The FASEB Journal* (Abstract No. 4689).

Evans, Gary W. (1989) *Int J Biosocial Med Research*, 11(2):163–180.

Khan et al. (1990) *Biological Trace Element Research* 24:183–188.

Stout, Robert W. (1985) *Metabolism*, 34(12 Suppl 1):7–12.

Striffler et al. (1995) *Metabolism*, 44(10):1314–1320.

Reid, Daniel (1990) *Chinese Herbal Medicine*, 150.

Renate Eisenhut et al.: "Medizinisch nutzbare wirkungen und inhaltstoffe von speisepepilzen." Gartenbauwissenschaft, vol. 56, No. 6, 1991, pp. 266–270, English Translation.

* cited by examiner

*Primary Examiner*—Christopher Tate
(74) *Attorney, Agent, or Firm*—Viola T. Kung

(57) ABSTRACT

This invention relates to potentiating insulin activity in a patient in need thereof. This invention provides a composition comprising an insulin potentiating agent; such composition comprises one or more substance derived from a water extract of *Polygonum multiflorum*, Agaricaceae, or *Cinnamomum mairei*. This invention also provides a method for treating hyperglycemia in a patient by administering to the patient an insulin potentiating agent. The method can be used to decrease blood glucose and/or glycosylated hemoglobin and/or glucose level.

12 Claims, No Drawings

COMPOSITION AND METHOD FOR INCREASING INSULIN ACTIVITY

TECHNICAL FIELD

This invention relates to a method of potentiating insulin activity. This invention is exemplified by the use of a composition comprising a substance derived from an aqueous extract of *Polygonum miultizorum*, Agaricaceae, and/or Cinnamomum.

BACKGROUND

Diabetes mellitus is a major public health problem. In the United States, there are approximately 8 to 10 million patients with diabetes. Diabetes is a syndrome that is caused by a relative or an absolute lack of insulin. Clinically, it is characterized by symptomatic glucose intolerance as well as alterations in lipid and protein metabolism. The maintenance of normal blood sugar levels is achieved by the actions of several hormones, most notably insulin, but also glucagon, epinephrine, corticosteroids, and growth hormone. Hypoglycemia, or low blood sugar, is characterized by below normal levels of blood glucose. On the other hand, hyperglycemia is exemplified by higher than normal concentrations of glucose in the blood. The pancreas produces insulin which is released in response to increased blood glucose concentrations. Insulin works to lower the blood sugar level by stimulating the uptake of glucose by cells. Glucose is used in cellular metabolism to produce energy, or is converted to glycogen for storage in the liver and muscles, or is used in the production of triglycerides and fats.

Hyperglycemia is associated with an increased risk for all of the common late complications of diabetes mellitus, which are the major causes of excess morbidity and mortality in diabetics. However, there is no generally applicable and consistently effective means of maintaining plasma glucose fluctuations within a normal range in diabetics, and efforts to do so entail significant risks of causing frequent or severe hypoglycemic episodes. Nevertheless, common treatments include diet management and the use of insulin preparations and oral hypoglycemic agents.

Conventional treatments for diabetes include oral hypoglycemia agent treatments. The two historically used classes of oral hypoglycemic agents are biguanides and sulfonylureas. Biguanides, however, are not currently approved for treatment of diabetes in the United States. Hypoglycemia is the most important complication of sulfonylurea treatment. Sulfonylurea-induced hypoglycemia can be severe and may last or recur for days after treatment is stopped. A mortality rate of 4.3% in patients hospitalized with sulfonylurea-induced hypoglycemia has been reported. Conventional insulin treatment for diabetes also include one or two injections per day of intermediate-acting insulin, with or without smaller added doses of rapid-acting insulin in the same syringe. Complications of insulin treatment include severe hypoglycemia, local allergic reactions, generalized insulin allergy, immunologic insulin resistance and local fat cell atropy or hypertrophy.

A composition which consists of a Sephadex G-25 column fraction isolated from a 0.1N ammonium hydroxide (base) extract of *Polygonum multiflorum* has been disclosed for treating hyperglycemia (U.S. Pat. No. 5,531,991). *Polygonum multiflorum* is also known as HeShouWu, or Chinese Cornbind. The natural distribution of *P. multiflorum* is in southwestern China, Japan, and Taiwan. It also has been reported to be effective against high blood pressure and hardening of the veins and arteries. (*Chinese Herbal Medicine*, McClellan Maitland Eds. (1990) p. 150). The disadvantages of using a base extract include that handling base in the manufacturing procedure is hazardous and should be avoided if possible. Furthermore, additional acidic components from the raw material are extracted. The acidic components increase the impurities in the extract and are not useful for human or animal consumption without further modification.

Considering the complications attendant to the use of insulin preparations and sulfonylureas in controlling blood glucose concentrations, there is a need for a new method and a new composition for treating hyperglycemia to control the high blood glucose levels associated with glucose intolerance. The new composition ideally is easy to manufacture and relatively inexpensive.

Relevant Literature

Chinese herbs have long been used in the treatment of many diseases. Modern day descriptions of Chinese herbs and their traditional usage can be found in Lu, Henry C., *Legendary Chinese Healing Herbs* (1991) and Reid, Daniel P., *Chinese Herbal Medicine* (1990).

U.S. Pat. No. 5,531,991 discloses a composition which consists of a Sephadex G-25 column fraction isolated from a 0.1N $NH_4OH$ extract of *Polygonum multiflorum*; and a method of using such a composition for treating hyperglycemia. Cheng et al (*FASEB* J. 2, A1103, 1988) report that the He Shou Wu (*Polygonum multiflorum*) extracted by 0.1 N $NH_4OH$ (1:20 dilution) has both an insulin-potentiating and a hypocholesterolemic effect in mice. Both references disclose a base extract of *Polygonum multiflorum*, but not a water extract. Kahn et al (*Biol. Trace Element Res.* 24, 183 (1990) disclose that the supernatant of cinnamon spice extracted with 0.1 N $NH_4OH$ (1:20, W/V) contains insulin potentiating activity.

U.S. Pat. No. 5,607,679 discloses a method of treatment of a skin disease associated with hyperproliferation of keratinocytes by administering to a patient an effective amount of *Agaricus bisporus* lectin. U.S. Pat. No. 5,639,470 discloses a method of deodorizing an animal comprising preparing a deodorant composition by a process of extracting *Agaricus bisporus* with a hydrophilic solvent to obtain an extract capable of deodorizing the animal; contacting said extract with a suitable carrier; and causing the animal to ingest said extract and said suitable carrier. Neither of the two references relates to insulin potentiating activity.

U.S. Pat. No. 5,175,156 discloses a method for treating undesirably high levels of blood serum lipids in an individual using a composition consisting essentially of chromium tripicolinate. Striffer et al (*Metabolism*, 44:1314:1320 (1995) report that chromium supplementation prevents insulin-secretory hyper-responsiveness produced in rats fed with a high-sucrose, low chromium diet and conclude that dietary chromium is required for maintenance of normal glucose tolerance in rats. Evans (*Int. J. Biosocial Med Res.* et al. 11: 163–180 (1989)) report that oral chromium supplements alone provide an improvement of insulin function in the non-diabetic animal. Chromium has been reported to potentiate insulin action, decrease glucose intolerance, decrease total cholesterol, LDL-cholesterol and triglyceride levels and increase HDL-cholesterol level (Anderson, *J. Adv. Medicine* 1:34–47 (1995).

SUMMARY OF THE INVENTION

This invention relates to a method and a composition for potentiating insulin activity in a patient in need thereof, such as a hyperglycemia patient. The method comprises administering to a patient an insulin potentiating agent that contains an effective amount of a natural substance derived from an aqueous extract of *Polygonum multiflorum*, Cinnamomum, and/or Agaricaceae. Optionally, trivalent chromium can be used in combination with the extracts of Polygonum, Cinnamomum, and/or Agaricaceae to enhance the effect. The invention also provides a composition comprising an insulin potentiating agent and a method of preparing the composition. The compositions find use in the treatment of hyperglycemia to lower blood glucose and glycosylated hemoglobin levels.

DETAILED DESCRIPTION OF THE PREFERRED EMBODIMENT

This invention relates to a method and a composition for potentiating insulin activity to treat hyperglycemic patients by lowering blood glucose levels and/or glycosylated hemoglobin levels. The compositions that are employed in this invention exhibit an insulin potentiating activity, i.e. they increase apparent insulin activity as measured by increased glucose uptake by cells. Improved insulin activity leads to decreased circulating insulin, which leads to lower blood glucose and lower glycosylated hemoglobin levels in patients; it also has an effect on smoothing out fluctuations in glucose levels. The decrease in circulating insulin further leads to a decrease in atherosclerosis. (Stout, (1985) *Metab.* 34:7–12). Total cholesterol, LDL-cholesterol and triglyceride levels in blood are decreased; and HDL-cholesterol levels are increased by administering an insulin potentiating agent.

The insulin potentiating agents are natural substances derived from an aqueous extract from plants or fungi such as mushrooms, and are safely consumed by humans. Therefore, the treatment of hyperglycemia patients with such naturally derived agents has the advantage that it does not cause side effects such as those caused by sulfonylurea. The use of these agents in conjunction with conventional drug treatments such as an oral hypoglycemia agent or insulin permits the use of lower doses of the drug and/or decreased frequency of administration which decreases the side effects most commonly observed with these treatments.

Insulin potentiating activity in potential sources of extracts is determined using any of a variety of tests, including, for example, using fat cell assays. Fat cells are prepared from rat epididymal fat pads. Samples or water control are incubated with $^{14}$C-glucose, albumin, dextrose and fat cells. Glucose uptake by cells is determined by the amount of $^{14}CO_2$ generated. Insulin potentiation is calculated by dividing the radioactive $CO_2$ released in the presence of sample by that released in response to water control. For example, an insulin potentiating activity (IPA) of 1 indicates that the sample tested had no measurable effect on insulin action and has no insulin potentiating activity whereas an IPA of >1 shows a measurable insulin potentiating activity in a fat cell assay.

A preferred source for preparing IPA-containing extracts is mushrooms which bear basidia on their gills in the family of Agaricaceae such as *Agaricus bisporus, Agaricus campestris, Agaricus arvensis, Agaricus xanthodermus, Agaricus nivesens, Agaricus bitorquis, Agaricus silvicola, Agaricus comtulus* and *Agaricus praeclaresquamosus*. The preferred species is *Agaricus bisporus*, which includes cultivars of this species such as Crimini and Portabella mushrooms. *Agaricus bisporus* is a white mushroom naturally distributed in Europe, North America, and China. *Agaricus bisporus* is edible and is prepared for food consumption by commercial companies. Another preferred source is plants in the family of Polygoncease; the preferred source is a Chinese herb *Polygonum multiflorum*. Another preferred source is bark from a cinnamon tree, in the family of Cinnamomum. The preferred species are *Cinnamomum mairei, Cinnamomum zeylanicum,* and *Cinnamomum cassia. Cinnamomum mairei* is a tree with highly aromatic bark, which bark can be used for preparing extracts. Commercial cinnamon bark which is the dried inner bark of the shoots and ground cinnamon obtained from the grocery store can also be used for preparing extracts.

The putative source tissue for insulin potentiating activity is obtained either as a ground powder or is prepared by cutting the plant or fungal tissue into small pieces, pulverizing it, grinding it or otherwise increasing the surface area of the pieces of tissue to facilitate extraction. Hydrophilic solvents are used for extraction of insulin potentiating activity from a potential source. Because it is safe, easy to use, and economic, distilled water is a preferred solvent for extraction. In addition, water does not extract those impurities soluble only in acid or base. A small amount of buffer can be added to the distilled water to maintain the pH. A small amount of ethanol or methanol also can be added to the distilled water as a solvent for extraction. However, high concentrations, such as 50%, of ethanol can extract undesired organic impurities, for example, cinnamic aldehyde from Cinnamomum, which is toxic in large amounts for human consumption. Furthermore, ethanol or methanol in the extract generally needs to be diluted to less than 1% before the extract is measured for activity, otherwise the ethanol/methanol can inhibit the insulin potentiating activity measured in the assay used to measure activity. The amount of solvent added to the raw material for extraction is, in general, in a volume ranging from 2–200 times per unit weight of the raw material, and preferably 20–100 times per unit weight.

Other solvents which can be used include dilute acids and bases. Dilute acids, such as acetic acid and hydrochloric acid also can be used: the acid concentration should be less than about 1 N, and preferably less than 0.5 N. For example, 0.1 N acetic acid or 0.1 N hydrochloric acid can be an effective solvent. Dilute bases, for example, ammonium hydroxide or sodium hydroxide, can be used as a solvent; the concentration of the base should be less than about 1 N and preferably less than 0.5 N. For example, 0.1 N $NH_4OH$ can be used as an effective solvent to extract insulin potentiating activity.

The insulin potentiating activity is temperature stable, and is not affected by the extraction temperature. The extraction therefore can be performed at a wide range of temperatures, but preferably at a temperature range from room temperature to about 100° C., for from about 15 minutes to overnight. The extraction is most preferably carried out by boiling the material to be extracted for from 10 minutes to one hour because the boiling procedure sterilizes the raw material. Extraction also can be performed at room temperature for from about 20 minutes to five hours. Extraction at 4° C. can be done, but is less practical because of its low efficiency of extraction.

After extraction, the liquid which contains the insulin potentiating activity is separated from any solid debris by centrifugation at a minimum of 1000×g for 20 minutes. Alternatively, the solution is filtered through a filter paper or a microfilter to remove any solid debris. If acid or base is used as the solvent for extraction, the extract usually is neutralized before further usage. The acidic or basic extract also may require a purification step to remove the undesirable acid or base soluble impurities before further usage.

The liquid extracted from the plant or fungal tissue source, which is free of solid debris, can be used directly as an insulin potentiating agent, or the liquid extract can be lyophilized or dried to form a powder. The liquid or the powder can be incorporated into a variety of basic materials in the form of a liquid, powder, tablets, or capsules to give an insulin potentiating activity effective to decrease blood glucose levels or glycosylated hemoglobin levels. Such a compound is effective in lowering blood glucose and glycosylated hemoglobin levels, and is effective in the treatment of hyperglycemia.

The liquid extract can further be purified using methods known in the arts such as ion exchange chromatography, molecular exclusion chromatography, affinity chromatography, HPLC, gel electrophoresis, etc., to obtain a compound that exhibits high insulin potentiating activity in a fat cell assay. Such a compound can be used as a structural model for designing other compounds which exhibit insulin potentiating activity.

While it is possible for the insulin potentiating agent to be administered alone, it is preferable to formulate the active ingredient as a pharmaceutical formulation. The formulations of the present invention comprise at least one insulin potentiating agent, together with one or more acceptable carriers and optionally other therapeutic agents. Other therapeutic agents suitable for use herein are any compatible drugs that are effective for the intended purpose, or drugs that are complementary to those of the present agents. The formulations utilized in combination therapy may be administered simultaneously, or sequentially, such that a combined effect is achieved. Suitable pharmaceutically acceptable carriers are well known in the art and vary with the desired form and mode of administration of the pharmaceutical formulation. For example, they may include diluents or excipients such as fillers, binders, wetting agents, disintegrators, surface-active agents, lubricants and the like. Typically, the carrier is solid, liquid or vaporizable carrier, or combinations thereof. Typical unit dosage forms include tablets, pills, powders, solutions, suspensions, emulsions, granules, capsules, suppositories. Each carrier is phamarceutically acceptable in the sense of being compatible with other ingredients in the formulation and in being not injurious to the patient, i.e. the carrier is biologically acceptable and inert.

Formulations include those suitable for oral and parenteral (including subcutaneous, intramuscular, intravenous and intradermal) administration, with oral formulations being preferred. A preferred oral formulation is an encapsulated dry powder of a water extracted supernatant from *P. multiflorum*, Cinnamomurm, cinnamon, or *Agaricus bisporus*, or a mixture of one or more of these extracts. Chromium can optionally be added in the capsule with the insulin potentiating agent, generally in the form of chromium picolinate or chromium chloride to provide a synergistic effect or can be administered separately.

The formulations can be conveniently prepared in unit dosage form and can be prepared by any method known in the art of pharmacy. Such methods include the step of bringing into association the active ingredient with the carrier which may encompass one or more accessory ingredients. In general, the formulations are prepared by uniformly and intimately bringing into association the active ingredient with liquid carriers or finely divided solid carriers or both, and as necessary, shaping the product. Various unit dose and multidose containers, e.g., sealed ampules and vials, can be used, as is well known in the art.

For example, to prepare formulations suitable for injection, solutions and suspensions are sterilized and are preferably isotonic to blood. In making injectable preparations, carriers which are commonly used in this field are used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such s sodium chloride, glucose or glycerin can be added to make the preparations isotonic. The aqueous sterile injection solutions may further comprise oxidants, buffers, bacteriostats, and like additions acceptable for parenteral formulations.

For therapeutic use in a method of treating or controlling disease states or conditions involving hyperglycemia, a composition of the present invention is conveniently administered in the form of a pharmaceutical formulation comprising at least one insulin potentiating agent of the present invention, and a pharmaceutically acceptable carrier. The treatment with an insulin potentiating agent generally is combined with a conventional treatment such as an insulin treatment. For example, the administration of an insulin potentiating agent can follow treatment of a patient with exogenous insulin. Alternatively, the insulin potentiating agent treatment can be administered simultaneously with the insulin treatment. The formulation according to the invention can be administered for therapy by any suitable routes, including oral and parenteral (including intraperitoneal, subcutaneous, intramuscular, intravenous and intradermal) routes. It will be appreciated that the preferred route will vary with the condition and age of the patient, and how long-lasting the treatment is.

The invention provides a method of treating hyperglycemia in a patient comprising administering to a patient a therapeutically effective amount of the composition of this invention which comprises at least one insulin-potentiating agent of the present invention, and a pharmaceutically-acceptable carrier. An "effective amount" of an insulin-potentiating agent is the amount sufficient to increase an insulin response in a hyperglycemic individual and is best determined empirically for each patient by monitoring long term glycemic control, because individual responses to treatment may vary, as is well known to those of skill in the art of treating hyperglycemia. An initial daily effective amount of an insulin potentiating agent for treating hyperglycemia patients is in general between 1,000 to 100,000 IPA units, preferably between 5000 to 50,000 IPA units, and more preferably between 20,000 and 50,000 IPA units, which dosage can be adjusted up or down depending upon the response of the individual hyperglycemic patient. The effective amount will vary depending upon several factors, including, but not limited to, the age and weight of the patient, the type of the disease state treated, how advanced the disease state is, the general health of the patient, the severity of the symptoms, whether the insulin potentiating agent is being administered alone or in combination with other therapies or other active ingredients, the incidence of side effects and the like. Generally, hyperglycemic patients take 1–10 capsules containing insulin potentiating agent daily for treatment. Each capsule contains 100–500 mg of dry powder of water extract supernatant from *P. multiflorum*, Cinnamomum, Agaricae, or a mixture thereof. Chromium picolinate, in an amount of about 100–300 $\mu$g, usually about 200 $\mu$g, also can be can be added into the capsule to elicit a synergistic effect. The amount of one or more active ingredients, i.e., the dry powder from the water extract free of solid debris, that is administered to a patient, ranges from 100–5000 mg, preferably 200–2500 mg, and more preferably 500–1500 mg. The dry powder can be a single component of *P. multiflorum*, Cinnamomum, Agaricae, or a mixture thereof. The dry powder additionally can include 100–3000 μg of chromium picolineate. The treatment duration generally is about 1–4 months; the need for continued treatment is monitored for individual patients.

Several different methods are employed for establishing the response to treatment of hyperglycemia patients and for monitoring the amount of extract to be administered. Measurement of serum glycosylated proteins, such as hemoglobin, is the most reliable method for assessing long-term glycemic control in people with diabetes (Bunn *Diabetes* 30:613–617 (1981); MacDonald *Human Pathol.* 10:279–291 (1979); Mayer et al *Clin. Chim. Acta.* 127:147–184 (1983); Schleicher et al *J. Clin. Chem. Clin. Biochem.* 27:577–587 (1989); Takara et al *Diabetes Care* 16:1313–1314 (1993); Takara et al *Diabetes Care* 18:440–447 (1995)). Hemoglobin $A_{1c}$ was originally postulated to reflect the simple mean plasma glucose level over a certain period. Considering the erythrocyte life span, glycosylated hemoglobin was thought to be uniformly accumulated in erythrocytes over 120 days. However, theoretical and experimental evidence demonstrate that following a consistent drop in blood glucose, the $HbA_{1c}$ changes rapidly in the first one to two months followed by a steady-state level after four months (see Takara et al, supra (1993); and Takara et al, supra (1995)). Seventy-five percent (75%) of the $HbA_{1c}$ level is proportional to the changes in blood glucose over the first two months. Two hour fasting blood glucose levels and serum insulin measurements are other methods which can be used to establish the effectiveness of treatment in individual patients with the insulin potentiating agent and to monitor the amount of agent to be administered. Blood glucose, hemoglobin $A_{1c}$ and insulin levels of patients are measured at time zero and every thirty days by methods known to those skilled in the art. For example, glucose is analyzed by glucose oxidase method (Loft et al *Clin. Chem* 21:1754–1760 (1975)). Insulin is measured by radioimmunoassay (Albano et al *Ecta Endrocrinol.* 70:487–509 (1972)). Hemoglobin $A_{1c}$ is measured using BioRad $HbA_{1c}$ columns (BioRad, Hercules, Calif.). A decrease in blood glucose, hemoglobin $A_{1c}$ and insulin indicate the effectiveness of treatment.

The extracts also find use in lowering total cholesterol, LDL-cholesterol and triglyceride levels, and in increasing HDL-cholesterol levels. The effect of the insulin potentiating agent on serum lipid levels is determined by measuring total cholesterol (Deacon et al, *Clin. Chem.* 25:976–984 (1979)), HDL cholesterol (Warnick et al, *Am. J. Clin. Nutr.* 78:718–723 (1982)), and triglyceride (Kohimeier, *Clin. Chem.* 32:63–66 (1986)) levels.

The following examples are presented as illustrations, not limitations.

EXAMPLES

Example 1

Assay for Measuring Potentiating Activity (a) Preparation of Isolated Fat Cells

Plastic containers were used exclusively for fat cell isolation and assay. Two rats were sacrificed by decapitation and their epididymal fat pads removed. The distal portion of the fat pads (about 2 g) was rinsed with 0.9% NaCl, minced with scissors, and incubated at 37° C. for 40–45 min in 10 mL of Krebs Ringer Phosphate (KRP) buffer containing 2 mg/ml of collagenase (CLS 47B177P, Worthington, Freehold, Mass.) in a water bath shaker at 150 rpm. The KRP contained 118 mM NaCl, 5 mM KCl, 1.3 mM $CaCl_2$, 1.2 mM $MgSO_4$, 1 mM $KH_2PO_4$, and 16.2 mM $Na_2HPO_4$ (pH 7.4). The digested tissue was passed through a silk screen (Adcom, Bethesda, Md.) using a 10 mL syringe. The preparation was then washed three times by centrifugation with KRP containing 2% albumin (Fraction V, Lot No. R53808, Armour Pharmaceutical Co., Kankakee, Ill.). Both KRP and KRP-albumin were millipore filtered and gased with $O_2$. The material below the floating fat cells and any fat above the adipocytes were removed by aspiration. KRP-albumin (9 mL) was added to disperse the washed fat cells. Fat cells remained viable for at least 4 h.

(b) Glucose Oxidation Studies.

25 μl of samples or 25 μl of water control were added to tubes that contained 1.9 mL of KRP-albumin, 0.4 μCi $C^{14}$-glucose (313 Ci/mol), and 68 μg of dextrose. Adipocytes (100 μl) were added, and caps containing center wells (Kontes) were used to seal the tubes. After incubation for 90–120 min at 37° C. and shaking at 150 rpm, 0.2 mL of hyamine hydroxide (10×) (Packard) was added to the center well, and 0.3 mL of 1.5 N $H_2SO_4$ was injected into the incubation mixture to stop the reaction. The tubes were incubated for 30 min to allow the hyamine to trap $^{14}CO_2$. The center wells were removed, carefully wiped, and added to 10 mL of Aquasol II (New England Nuclear, Mass.) and counted in a Beckman Liquid Scintillation Counter. Insulin potentiation activity was calculated by dividing the radioactive $CO_2$ released in the presence of sample by that released in response to water control. An insulin potentiating activity (IPA) of 1 indicates that the sample tested had no measurable effect on insulin action.

Example 2

Water Extraction of *Polygonum multiflorum*

Roots of *P. multiflorum* were cut up and ground into small pieces. 100 ml of distilled water was added to 1 g of *P. multiflorum*. The mixture was stirred for 25 minutes at room temperature, and then centrifuged at 1,200×g for 20 minutes to remove the debris. The supernatant was collected and assayed for insulin potentiating activity at different dilutions according to the procedures of Example 1. The IPAs of undiluted, 1:2 and 1:10 dilutions of supernatant were 3.8, 4.8 and 1.1 respectively. After the supernatant was dried for at least 3 to 4 hours in a 50° oven, 1 ml of the supernatant yielded a dry powder of 4.4 mg by weight. The insulin potentiating activity of the dry powder is 87 IPA/mg.

Example 3

Water Extraction of *C. mairei*

Bark of *C. mairei* was cut up and ground into small pieces. 100 ml of distilled water was added to 1 g of *C. mairei*. The mixture was stirred for 25 minutes at room temperature, and then centrifuged at 1,200×g for 20 minutes to remove the debris. The supernatatant was collected and assayed for insulin potentiating activity at different dilutions according to Example 1. The IPAs of undiluted, 1:2 and 1:10 dilutions of supernatant were 2.3, 3.6 and 3.8. After the supernatant was dried for at least 3–4 hours in a 50° oven, 1 ml of the supernatant yielded a dry powder of 1.6 mg by weight. The insulin potentiating activity of dry powder is 950 IPA/mg.

Example 4

Water Extraction of *Agaricus bisporus*

Commercial *Agaricus bisporus* powder "Bai Bao" (Xiamen Torch Bio-Tech Co. Ltd., China) was used in this example. Bai Bao is a by-product of the procedure used for canning. Before *A. bisporus* (mushrooms) are put into cans, they are boiled in water. After boiling, the mushrooms are removed, and the water extract is dried into a powder which is the Bai Bao product. Bai Bao was used directly in the extraction procedure. 20 ml of water was added to 1 g of dry Bai Bao powder. The mixture was shaken at room temperature for 1 hour, and then centrifuged at 1,200×g for 20 minutes to remove any debris. The supernatant was collected and assayed at different dilutions for insulin potentiating activity as described in Example 1. The IPAs of the undiluted, 1:5 and 1:10 supernatant were 4.2, 2.9 and 2.1. After the supernatant was dried for at least 3 to 4 hours in a 50° oven, 1 ml of the supernatant yielded a dry powder of 23.2 mg by weight. The insulin potentiating activity of the dry powder is 25 IPA/mg.

Example 5

Insulin Potentiating Activity of Mixtures of Different Extracts

Chromium tripicolinate (Nutrition 21, San Diego, Calif.) was dissolved in distilled water to a concentration of 6.4 mg/ml. An equal volume mixture of (a) water extract of *P. multiflorum* (1:2 diluted supernatant of Example 2), (b) *C. mairei* (1:10 diluted supernatant of Example 3), (c) *A. bisporus* (undiluted supernatant of Example 4) or (d) chromium tripicolinate solution (6.4 mg/ml in water) was prepared. The insulin potentiating activity of the mixture was measured by testing 25 μl of each of the mixtures according to the procedure of Example 1. The results are summarized in Table 1.

TABLE 1

IPA of different extracts

| Sample | IPA |
|---|---|
| (a) *P. multiflorum* + (b) *C. mairei* | 3.5 |
| (b) *C. mairei* + (c) *A. bisporus* | 7.0 |
| (a) *P. multiflorum* + (c) *A. bisporus* | 5.2 |
| (b) *C. mairei* + (c) *A. bisporus* + (d) chromium | 4.7 |
| Water control | 1.0 |

Example 6

Animal Study of Effectiveness of Insulin Potentiating Agent 1 g. of *Agaricus bisporus*, *C. mairei*, *Polyflorum multiflorum*, or a combination of *Agaricus bisporus* and *C. mairei* and *P. multiflorum* or *A. bisporus* and *C. mairei* are extracted with 5–100 ml of distilled water according to the protocols in Examples 2–4. Twenty to forty male weanling mice are randomly assigned to seven groups as listed in Table 2 for treatment. Each mouse is given 100 μl of water extract of tissues or water control orally by micropipette daily with or without chromium picolineate. The treatment duration is one to two months. Blood glucose, hemoglobin $A_{1c}$ and insulin levels are measured in each mouse at time zero, and at the end of one and two months. Glucose is analyzed by the glucose oxidase method (Loft et al, *Clin. Chem.* 21:1754–1760 (1975). Insulin is measured by radioimmunoassay (Albano et al *Ecta Endocrinlol.* 70:487–509 (1972). Hemoglobin $A_{1c}$ is measured using BioRad $HbA_{1c}$ columns (BioRad, Hercules, Calif.).

TABLE 2

Treatment of Mice with different water extracts of Chinese herbs

| Group | Tissue |
|---|---|
| I | *P. multiflorum* |
| II | *C. mairei* |
| III | *A. bisporis* |
| IV | *A. bisporis* and *C. mairei* (1:1 by weight) |
| V | *A. bisporis* and *C. mairei* and *P. multiflorum* (1:1:1 by weight) |
| VI | *A. bisporis* and *C. mairei* (1:1 by weight) plus 200 μg chromium picolineate |
| VII | no active ingredient |

Example 7

Pilot Clinical Study

People of 35–65 years of age, free of disease other than Type II diabetes, with a fasting blood glucose of 7.2–15.5 mmol/L, 2-hour blood glucose of 9.4–16.7 mmol/L and a hemoglobin $A_{1c}$ of 8.0–12%, are selected for pilot study. Patients continue their regular treatment for diabetes, for example, sulfonylurea drugs, insulin, or no medication.

Each of seven groups of patients each take different capsules. There are 3–5 patients in each group and they are each treated for 1–3 months with 1–10 capsules containing 200–500 μg dry extract powder per day administered orally. The capsules taken by each group contain dried powder of water extract of *P. multiflorum*, *C. mairei*, or *bisporis* and chromium picolineate. A control group will take placebo capsules (see following table).

TABLE 3

Treatment of human with capsules containing different insulin potentiating agent

| Group | Capsule Content |
|---|---|
| I | *P. multiflorum* |
| II | *C. mairei* |
| III | *A. bisporis* |
| IV | *A. bisporis* and *C. mairei* (1:1 by weight) |
| V | *A. bisporis* and *C. mairei* and *P. multiflorum* (1:1:1 by weight) |
| VI | *A. bisporis* and *C. mairei* (1:1 by weight) plus 200 μg chromium picolineate |
| VII | no active ingredient |

Blood glucose, hemoglobin $A_{1c}$ insulin, total cholesterol, HDL cholesterol and triglycerides are measured in each patient at time zero, one, two and three months. Blood glucose, insulin and hemoglobin $A_{1c}$ are measured as described in Example 6. Total cholesterol is determined by chemical hydrolysis (Deacon et al *Clin Chem* 25:976–984 (1979)), HDL cholesterol by phosphotungstate-Mg precipitation (Warnick et al, *Am. J. Clin. Nutr.* 78:718–723 (1982)) and triglycerides by direct enzymic measurement (Kohimeier, *Clin. Chem.* 32:63–66 (1986)). Blood urea nitrogen BUN is determined by a direct method (aoster et al, *Clin. Chem.* 17:921–925 (1971)).

Example 8

Clinical Study

People being treated for diabetes are screened to obtain 100–200 subjects fitting the selection criteria. The selection criteria include that the subjects are free of disease other than type II diabetes, 35–65 years of age, have a fasting blood glucose of 7.2–15.5 mmol/L, 2-hour blood glucose of 9.4–16.7 mmol/L and a hemoglobin $A_{1c}$ ($HbA_{1c}$) 8.0–12%. Subjects are adults of normal height, weight and body mass index with diabetes for less than ten years. Patients continue their regular treatment for diabetes, for example, sulfonylurea drugs, insulin, or no medication.

The subjects with diabetes who meet the selection criteria are randomly divided into seven groups as listed in Table 3 above. Subjects are instructed to take 1–10 capsules per day (see Example 7) of their particular test agent. Subjects are also urged to maintain their normal eating and exercise habits. Subjects continue their normal visits to monitor their diabetes. A fasting blood sample and a blood sample following a two-hour glucose challenge (75 g of glucose) are obtained at the beginning of the study and after two and four months of treatment. Data for all subjects who complete all phases of the study are included in all of the respective analyses.

The study design is double-blind, placebo controlled. Placebo capsules are indistinguishable from those containing test agents. Blood glucose, insulin, hemoglobin $A_{1c}$, total cholesterol, HDL cholesterol, triglyceride and blood urea nitrogen are measured as described in Example 7.

The variables, $HbA_{1c}$ fasting and 2-hour glucose, insulin, total cholesterol, HDL cholesterol, triglyceride and blood urea nitrogen are analyzed as three factor repeated measures mixed linear models using PROC MIXED (SAS Institute, Cary, N.C.). Since the variables are measured at 0, 2 and 4 months for each subject, repeated measure analyses are used.

The above examples demonstrate methods of preparing water extracts of *P. multiflorum, C. mairei*, and *A. bisporus* and a method of measuring insulin potentiating activity in vitro. The examples also demonstrate that the subject water extracts of *P. multiflorum, C. mairei*, and *A. bisporus* have high insulin potentiating activities in an in vitro fat cell assay.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A method for decreasing the glycosylated hemoglobin level or blood glucose level in a hyperglycemic patient, said method comprising:

administering to said patient a composition comprising an effective amount of a water extract or a dilute acidic extract of *Polygonum multiform* roots or Cinnamomum bark, or a mixture thereof, wherein said extract is administered in an amount sufficient to potentiate insulin activity in said hyperglycemic patient, whereby said glycosylated hemoglobin level or said blood glucose level is decreased as compared to levels prior to treatment.

2. The method according to claim 1, wherein said administering is following treatment with exogenous insulin.

3. The method according to claim 1, wherein said method further comprises administering insulin to said hyperglycemic patient.

4. The method according to claim 1, wherein said method further comprises administering another oral hypoglycemic agent to said hyperglycemic patient.

5. The method according to claim 1, wherein said composition is in a dry powder form.

6. The method according to claim 5, wherein said composition comprises 100–5000 mg of dry weight of said extract.

7. The method according to claim 5, wherein said composition further comprises a trivalent chromium salt.

8. The method according to claim 7, wherein said chromium salt is chromium tripicolinate in an amount of 100–300 µg.

9. The method according to claim 1, wherein said composition further comprises a pharmaceutically acceptable carrier.

10. The method according to claim 1, wherein said extract is a water extract.

11. The method according to claim 1, wherein said composition further comprises a water extract of Agaricaceae.

12. The method according to claim 1, wherein said composition further comprises a trivalent chromium salt.

* * * * *

(12) EX PARTE REEXAMINATION CERTIFICATE (8963rd)
United States Patent
Cheng

(10) Number: US 6,200,569 C1
(45) Certificate Issued: Apr. 17, 2012

(54) COMPOSITION AND METHOD FOR INCREASING INSULIN ACTIVITY

(75) Inventor: Nanzheng Cheng, Beijing (CN)

(73) Assignee: Tang-An Medical Co., Ltd., Beijing (CN)

Reexamination Request:
No. 90/010,465, Apr. 24, 2009

Reexamination Certificate for:
Patent No.: 6,200,569
Issued: Mar. 13, 2001
Appl. No.: 08/965,051
Filed: Nov. 5, 1997

(51) Int. Cl.
*A61K 38/28* (2006.01)
*A61K 9/48* (2006.01)
*A61K 33/24* (2006.01)
*A61K 36/00* (2006.01)
*A61K 36/07* (2006.01)
*A61K 36/54* (2006.01)
*A61P 3/10* (2006.01)
*A61P 43/00* (2006.01)
*A61P 3/00* (2006.01)

(52) U.S. Cl. .............. 424/739; 424/655; 424/763; 514/866; 514/184; 514/5.9; 514/6.8; 514/13.5; 530/371

(58) Field of Classification Search .................. None
See application file for complete search history.

(56) References Cited

To view the complete listing of prior art documents cited during the proceeding for Reexamination Control Number 90/010,465, please refer to the USPTO's public Patent Application Information Retrieval (PAIR) system under the Display References tab.

*Primary Examiner* — Bruce Campell

(57) ABSTRACT

This invention relates to potentiating insulin activity in a patient in need thereof. This invention provides a composition comprising an insulin potentiating agent; such composition comprises one or more substance derived from a water extract of *Polygonum multiflorum*, Agaricaceae, or *Cinnamomum mairei*. This invention also provides a method for treating hyperglycemia in a patient by administering to the patient an insulin potentiating agent. The method can be used to decrease blood glucose and/or glycosylated hemoglobin and/or glucose level.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Colum 10, lines 27-*34:*

Each of seven groups of patients [each take] *takes* different capsules. There are 3-5 patients in each group and they are each treated for 1-3 months with 1-10 capsules containing 200-500 [μg] *mg* dry extract powder per day administered orally. The capsules taken by each group contain dried powder of water extract of *P. multiflorum, C. mairei,* or *bisporis* and *chromium picolineate.* A control group will take placebo capsules (see following table).

AS A RESULT OF REEXAMINATION, IT HAS BEEN DETERMINED THAT:

Claims 3, 4, 7 and 8 are cancelled.

Claims 1, 6 and 9-12 are determined to be patentable as amended.

Claims 2 and 5, dependent on an amended claim, are determined to be patentable.

New claims 13-24 are added and determined to be patentable.

1. A method for decreasing the glycosylated hemoglobin level or blood glucose level in a hyperglycemic patient, said method comprising:

administering to said patient a composition [comprising] *having an active ingredient consisting essentially of* an effective amount of a *non-acidic, non-basic* water extract or a dilute acidic extract of [Polygonum multiform roots or] Cinnamomum bark, [or a mixture thereof,] wherein said extract is administered in an amount sufficient to potentiate insulin activity in said hyperglycemic patient, whereby said glycosylated hemoglobin level or said blood glucose level is decreased as compared to *the* levels prior to treatment.

6. The method according to claim 5, wherein said [composition comprises] *active ingredient consisting essentially of* 100-5000 mg of dry weight of said extract.

9. The method according to claim 1, wherein said [composition further comprises] *non-acidic, non-basic water exract or a dilute acidic extract of Cinnamomum bark is formulated in* a pharmaceutically acceptable carrier.

10. The method according to claim 1, wherein said [extract is a] *active ingredient consists essentially of a non-acidic, non-basic* water extract of *Cinnamomum bark.*

11. [The method according to claim 1, wherein said composition further comprises] *A method for decreasing the glycosylated hemoglobin level or blood glucose level in a hyperglycemic patient, said method comprising:* administering to said patient a composition having active ingredients consisting essentially of an effective amount of a non-acidic, non-basic water extract of Cinnamomum bark and a water extract of Agaricaceae, wherein said composition is administered in an amount sufficient to potentiate insulin activity in said hyperglycemic patient, whereby said glycosylated hemoglobin level or said blood glucose level is decreased as compared to the levels prior to treatment.

12. [The method according to claim 1, wherein said composition further comprises] *A method for decreasing the glycosylated hemoglobin level or blood glucose level in a hyperglycemic patient, said method comprising:*

*administering to said patient a composition having active ingredients consisting essentially of an effective amount of a non-acidic, non-basic water extract of Cinnamomum bark and a trivalent chromium salt, wherein said composition is administered in an amount sufficient to potentiate insulin activity in said hyperglycemic patient, whereby said glycosylated hemoglobin level or said blood glucose level is decreased as compared to the levels prior to treatment.*

*13. The method according to claim 12, wherein said chromium salt is chromium tripicolinate in an amount of 100-300 μg.*

*14. The method according to claim 10, wherein said composition is in a dry powder form.*

*15. The method according to claim 14, wherein said non-acidic, non-basic water extract of Cinnamomum bark is in an amount of 100-5000 mg of dry weight.*

*16. An method for decreasing the glycosylated hemoglobin level or blood glucose level in a hyperglycemic patient, said method comprising:*

*administering to said patient a composition having active ingredients consisting essentially of an effective amount of a non-acidic, non-basic water extract of Cinnamomum bark and a non-acidic, non-basic water extract of Polygonum multiforum, wherein said composition is administered in an amount sufficient to potentiate insulin activity in said hyperglycemic patient, whereby said glycosylated hemoglobin level or said blood glucose level is decreased as compared to the levels prior to treatment.*

*17. An method for decreasing the glycosylated hemoglobin level or blood glucose level in a hyperglycemic patient, said method comprising:*

*administering to said patient a composition having active ingredients consisting essentially of an effective amount of a non-acidic, non-basic water extract of Cinnamomum bark, a non-acidic, non-basic water extract of Polygonum multiforum, and a trivalent chromium salt, wherein said composition is administered in an amount sufficient to potentiate insulin activity in said hyperglycemic patient, whereby said glycosylated hemoglobin level or said blood glucose level is decreased as compared to the levels prior to treatment.*

*18. The method according to claim 17, wherein said chromium salt is chromium tripicolinate in an amount of 100-300 μg.*

*19. The method according to claim 16, wherein said composition is in a dry powder form.*

*20. The method according to claim 19, wherein said non-acidic, non-basic water extract of Cinnamomum bark is in an amount of 100-5000 mg of dry weight.*

*21. The method according to claim 17, wherein said composition is in a dry powder form.*

22. The method according to claim 21, wherein said non-acidic, non-basic water extract of Cinnamomum bark is in an amount of 100-5000 mg of dry weight.

23. The method according to claim 11, wherein said non-acidic, non-basic water extract of Cinnamomum bark is in an amount of 100-5000 mg of dry weight.

24. The method according to claim 12, wherein said non-acidic, non-basic water extract of Cinnamomum bark is in an amount of 100-5000 mg of dry weight.

* * * * *